(12) United States Patent
Karita

(10) Patent No.: US 6,190,685 B1
(45) Date of Patent: Feb. 20, 2001

(54) ANTIOXIDIZING COMPOSITION FOR SCAVENGING FREE RADICALS, PHARMACEUTICAL COMPOSITION COMPRISING THE SAME, AND PROCESS FOR PREPARING THE SAME

(75) Inventor: Takeshi Karita, Shinjuku-ku (JP)

(73) Assignee: Takahisa Karita, Hokkaido (JP)

( * ) Notice: Under 35 U.S.C. 154(b), the term of this patent shall be extended for 0 days.

(21) Appl. No.: 09/269,270

(22) PCT Filed: Sep. 26, 1997

(86) PCT No.: PCT/JP97/03446

§ 371 Date: Mar. 25, 1999

§ 102(e) Date: Mar. 25, 1999

(87) PCT Pub. No.: WO98/13055

PCT Pub. Date: Apr. 2, 1998

(30) Foreign Application Priority Data

Sep. 27, 1996 (JP) .................................................... 8-256471

(51) Int. Cl.[7] ............................. A61K 9/70; A61K 35/78
(52) U.S. Cl. .................... 424/424; 424/195.1; 424/423; 424/425; 424/443; 424/444; 424/486
(58) Field of Search ............................... 424/195.1, 423, 424/425, 443, 444, 486

(56) References Cited

FOREIGN PATENT DOCUMENTS

| 2706294 | 12/1994 | (FR) . |
|---|---|---|
| 61-151131 | 7/1986 | (JP) . |
| 63-79834 | 4/1988 | (JP) . |
| 3-157334 | 7/1991 | (JP) . |
| 3-227938 | 10/1991 | (JP) . |
| 6-24937 | 2/1994 | (JP) . |
| 8-26980 | 1/1996 | (JP) . |
| 8-109137 | 4/1996 | (JP) . |
| 8-119869 | 5/1996 | (JP) . |
| 8-259452 | 10/1996 | (JP) . |

OTHER PUBLICATIONS

Computer Derwent Abstract 1998–364409[32]WPIDS Dimmeler DE–29806948, 1998.*
Computer Caplus Abstract 1987:38503 Simard FR2576212, 1998.*
Computer Caplus Abstract 1986:578220 Chudovskaya et al SU1247011, 1998.*
Chemical Abstracts, vol. 124, Abstract No. 269942 & J. Appl. Cosmetol., 13(2), 1995, pp. 27–34.
Chemical Abstracts, vol. 121, Abstract No. 26825 & Yaowu Shipin Fenxi, 1(4), 1993, pp. 357–64.
Mol. Cell. Biochem., 148(2), 1995, pp. 183–9.
Clinical Biochem., 27(5), 1994, pp. 319–32.
Calabrese et al Chemical Abstracts vol. 124 No. 20, May 13, 1996 124:266942s Evaluation of a lipid soluble fraction isolated from lemon oil extract etc.
Yang et al Chemical Abstracts vol. 121 No. 3, Jul. 18, 1994 121:26825q Garlic as anti–oxidants and free radical scavengers.
Prasad et al Molecular and Cellular Biochemistry 148: 183–189, 1995 Antioxidant activity of allicin, an active principle in garlic.
Stavric Clinical Biochemistry, vol. 27, No. 5, pp 219–332 Oct. 1994 Role of Chemoprevents in Human Diet.

* cited by examiner

*Primary Examiner*—Herbert J. Lilling
(74) *Attorney, Agent, or Firm*—Nixon & Vanderhye

(57) ABSTRACT

An anti-oxidizing composition for scavenging free radicals, comprising at least one essential oil component containing a number of fat-soluble, low-molecular-weight compounds, a pharmaceutical composition comprising the above composition, and a process for preparing the same are described. Percutaneous absorption of the pharmaceutical composition is effective in treating immune diseases, particularly AIDS.

4 Claims, 2 Drawing Sheets

ANTIOXIDIZING COMPOSITION FOR SCAVENGING FREE RADICALS, PHARMACEUTICAL COMPOSITION COMPRISING THE SAME, AND PROCESS FOR PREPARING THE SAME

This application is a 35 U.S.C. §371 of PCT/JP97/03446, filed Sep. 26, 1997.

FIELD OF THE INVENTION

The present invention relates to an antioxidizing composition for scavenging free radicals generated in a living body, a pharmaceutical composition comprising thereof, and a process for preparing thereof.

BACKGROUND OF THE INVENTION

Active oxygen or free radical causes various troubles in a living body. Active oxygen or free radical is generated by bacteria invasion into the living body, in chitin-chitosan oxidase system, arachidonic cascade system, or a process of saccharification, and so forth.

Active oxygen is a generic name of super hydroxy radical ($.O_2^-$), singlet oxygen ($^1O_2$) and hydroxy radical (.OH). Hydroxy radical is formed by taking an electron into the orbital of triplet oxygen in ground states. The singlet oxygen is defined as the oxygen wherein two unpaired electrons of an oxygen atom make a pair to enter orbital of the other oxygen atom, resulting the electron orbitals are empty.

Furthermore, perhydoxyradical (.OOH), which is a typical free radical, is generated when peroxide is decomposed by autoxidation via the following route.

$$RH + O_2 \rightarrow ROOH \rightarrow R. + .OOH$$

Perhydoxyradical looses a proton in alkaline solution to be converted to superoxide (.OO$^-$). In the living body, free dihydroflavin non-enzymatically reacts with oxygen very quickly to generate perhydroxy radical.

Perhydroxyradical is converted to the above-mentioned superoxide, and then superoxide is catalyzed by superoxide dismutase (SOD) to generate an oxygen molecule and hydrogen peroxide.

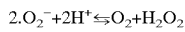

$$2.O_2^- + 2H^+ \leftrightarrows O_2 + H_2O_2$$

In the bacteria invasion, free radicals including active oxygen are generated to exclude extraneous material for the living body; after bacteria invade to the living body, neutrophils phagocytose such materials and release activated oxygen from their membrane. In chitin-chitosan oxidase system, serious tissue lesion occurs; in ischemia, active oxygen is generated by increasing hypoxanthine and xanthine oxidase level in cells, and after ischemia a larger amount of active oxygen is generated by introducing a lot of oxygen into the cells. Such tissue lesion is referred to as ischemia-perfusion disorder. In an arachidonic acid cascade system, unsaturated fatty acid is peroxidized through autoxidation mechanism to generate peroxides and radicals.

Since thus generated free radicals cause various diseases such as inflammation, allergy, cerebral nerve disease and tissue lesions, it is required that the excessive generation of free radicals should be prevented or the generated free radicals should be scavenged. Target molecules and lesions caused by damaging them are shown in Table 1.

TABLE 1

In vivo target molecule for active oxygen and free radicals

| Target molecules | Lesions |
|---|---|
| Lipids | Peroxidation and lesion of biomembrane |
| Nucleic Acids | Cell cycle change, mutation, DNA chain cleavage, base damage, carcinogenesis, and AIDS |
| Amino Acids | Denaturation of protein, polymerization, enzyme repression, and cross-linking denaturation |
| Carbohydrate | Change of cell surface receptor |
| Hyaluronic acid | Depolymerization |
| Biological Factors | Inactivation (α-antitrypsin, chemotactic factor, chemical mediator, neurotransmitter) |

Among the substances, which are biosynthesized in vivo, any substance capable of scavenging .OH is not known. In vivo, .OH is generated by reduction of $H_2O_2$ by using transition metal, decomposition of $H_2O$ upon irradiation and reaction of NO with superoxide. This .OH is highly reactive and reacts with almost all the biosubstance in a rate-determining manner by nucleic acids. Therefore, the .OH often gives a living body a mortal wound. Accordingly, in order to prevent or terminate such wounds, it is required to provide a substance having antioxidation activity for .OH from outside of the living body.

As active oxygen inhibitors, which are presently known, there can be mentioned ceruloplasmin, metallothionein and vitamin C. Ceruloplasmin is a plasma protein of which molecular weight is about 16,000, including 6 to 7 copper ions per molecule, and it is known that it shows SOD activity against $.O_2^-$. This protein is rich in blood, and it seems to be a scavenger of active oxygen ($.O_2^-$) in blood vessel. Metallothionein is a metalloprotein of which molecular weight is about 60,000, and cysteine occupies 30% of its structure protein. It is known that this protein scavenges hydroxy radicals (.OH) and suppresses peroxidation of lipids. Vitamin C is known as a scavenger for $.O_2^-$, .OH, singlet oxygen ($^1O_2$), hydrogen peroxide ($H_2O_2$), and so forth. These substances are used as pharmaceuticals, but all of them are water-soluble and have a relatively high molecular weight. Furthermore, they are mainly administered per os or via injection. They act as the scavengers in extracellular fluid, but are not incorporated into the cells.

In general, drugs are transferred into blood and then delivered to target sites by blood flow. Since fat-soluble drugs pass through blood-brain barrier (BBB) to be transferred into brain, such drugs have a trouble from the viewpoint of side effects. Therefore, water-soluble drugs are selected, and such administration routes are used. However, it is difficult to deliver the drug to the target sites with effective dose by transferring the drug in blood. Particularly, it is almost impossible to deliver the drug at such dose when the target site is lymph tissue.

Such drugs are desired to have a low molecular weight rather than a high molecular weight from the viewpoint of formulation or administration, and to be compounds or compositions having antioxidizing activity. As mentioned above, free radicals cause various diseases or tissue lesions, particularly peroxidation of lipid, to generate peroxides and radicals to influence badly for living body. Considering these matters, lymptropic drugs or compositions are needed.

However, lymptropic drug or compositions having antioxidization activities are not known. Particularly, those capable of preventing lipid peroxidization have not found.

On the other hand, it is known that enzymes such as SOD, catalase and glutathione peroxidase scavenge free radicals. Furthermore, as examples of antioxidizing substances, which are defined as the substances having antioxidization activities, a singlet oxygen scavenger, a superoxide scavenger, a hydroxy radical scavenger, and an antioxidizing of which mechanism is not clarified are known. Specifically, as examples of the singlet oxygen scavenger, there can be mentioned β-carotene, amines, tocopherols and histidines; as superoxide scavengers, tocopherols, phenols, thiols, ascorbic acid, and copper(II)-histidine complexes; as hydroxy radical scavengers, mannitol; and as the antioxidizing of which mechanism is not clarified, nucleic acid bases, fulavonoids, sterol, terpene, and polycarboxilic acid.

Accordingly, there are not effective means to scavenge free radicals at present, and only preventive means for free radical generation is used. In such preventive means, enzymes such as SOD, catalase and glutathione peroxidase, fat-soluble or water-soluble vitamins included in foods such as vitamin E, which is called tocopherol, vitamin A, vitamin D, vitamin C and vitamin Bs, and various coloring matters such as carotenoid which is fat-soluble coloring matters, and fulavonoid which is water-soluble coloring matters are taken parenterally or per os as antioxidizing substances.

Such compounds may be taken alone, or in combination; for example, several antioxidizing compounds such as tannin, flavonoid, carotenoid, vitamin C, caffeic acid derivatives, lignans and saponin which are included in Chinese orthodox crude drug used in Oriental medicine from ancient age.

In Chinese orthodox medicine, it is known that those antioxidizing compounds play great roles in action mechanism. However, since these compounds are water-soluble, there is a problem from the viewpoint of lymptropic activity.

When the above-mentioned antioxidizing enzymes or substances are taken per os, those enzymes are digested digestive tract or liver in absorption step to be metabolites, their bioavailability as drugs are not enhanced. Furthermore, if they are administrated parenterally, they are transferred into blood but not into lymph. Such tendency is also observed in the antioxidizing substance, vitamins described above.

SUMMARY OF THE INVENTION

Inventors of the present invention have studied eagerly to solve the problems mentioned above. They found that essential oil component including fat-soluble compounds with a low molecular weight have antioxidizing activity and at least one component in such essential oils are transferred into lymph at a high ratio when they are adsorbed percutaneously, and completed the present invention.

The first embodiment of the present invention is a free radical scavenging composition comprising at least one essential oil including a plurality of fat-soluble low-molecular-weight compounds, which is characterized as having antioxidization activity. The fat-soluble compounds are a straight or branched chain compound with 4 to 14 carbon atoms. The fat-soluble low-molecular-weight compound is selected from the group consisting of phenolic compounds from naturally occurring substance, sulfur-containing compounds, and terpenoid. Furthermore, the phenolic compounds are selected from the group consisting of thyme oil, an essential oil from Labiatae plants and that from Eucalyptus plants. Sulfur-containing compound is selected from the group consisting of garlic oil, welsh onion oil and scallion oil. The terpenoid is selected from the group consisting of lemon oil, an essential oil from Rutaceae plants and lavender oil.

The second embodiment of the present invention is a pharmaceutical composition containing the antioxidizing compositions described above. The pharmaceutical composition comprises the antioxidizing compound, a polymer resin, finely divided activated carbon particles, a porous substance, and a thermoplastic resin. The composition of the present invention may further comprise a coloring agent, a polysaccharide, a water-soluble resin, and so forth. The polymer resin is preferably an acrylic polymer having water absorption properties. The porous substance is preferably zeolite, and its pore size is preferably in the range of about 3 to about 10 Å. The coloring matter is preferably that which absorbs light with a wavelength in the range of 400 to 450 nm. The polysaccharide is preferably chitosan or cellulose. The thermoplastic resin is preferably polyethylene, and the water-soluble resin is polyvinyl alcohol (PVA).

In the second embodiment of the present invention, the pharmaceutical composition is inserted between two pieces of sheet materials. Then the whole edges of the pieces are bonded by heat pressing each other to form a percutaneous absorption agent. The sheet material is preferably made of paper or non-woven fabric. The pharmaceutical composition is preferably used for immune diseases, and especially for AIDS or autoimmune disease. Furthermore, the composition of the present invention is a composition applying for oxidation disorder.

The third embodiment of the present invention is a process for producing a pharmaceutical composition comprising the steps of adsorbing the antioxidizing composition onto the surface of each thermoplastic resin bead, forming an oil film on the antioxidizing composition-adsorbed resin surface, adsorbing finely divided carbon powder particles on the film-formed to form a capsule, preparing a base material by mixing together a polymer resin, a porous substance and a poly saccharide, and then mixing together the capsule, the base, and a coloring agent.

BRIEF DESCRIPTION OF THE DRAWINGS

As shown in FIG. 1, the $CD4^+$ and $CD8^+$ T cell numbers are increased quickly after administrating the present composition. When the administration of the present composition is stopped, both the cell numbers are decreased. However, the cell numbers are again greatly increased when the composition is administrated again.

Figure 1:
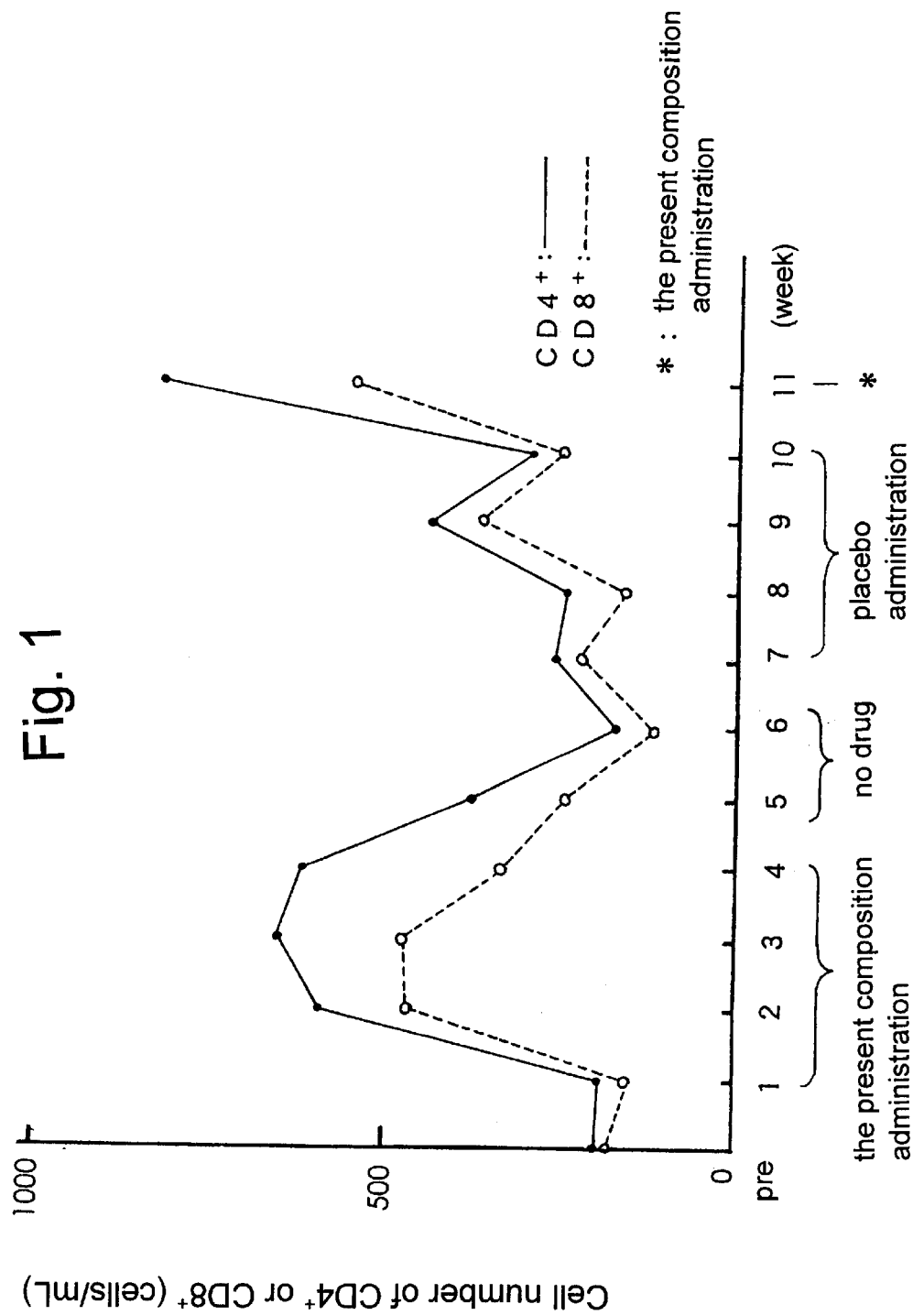
FIG. 1 is a graph showing the change of $CD4^+$ and $CD8^+$ T cell number when the pharmaceutical composition of the present invention or placebo is administrated to cats appearing AIDS symptoms.

The formation ratio of Heinz body is suppressed by administrating the present composition and there is a significant difference in the Heinz body formation ratios as observed 40 hours after.

MODE FOR CARRYING OUT THE INVENTION

The present invention will now be explained in detail hereinbelow.

The anti-oxidizing composition of the present invention comprises at least one essential oil component, which includes a plurality of fat-soluble compounds having a low molecular weight. The fat-soluble compounds contain 4 to 14 carbon atoms, and it may contain hetero atoms. These fat-soluble compounds may have a straight chain, branched chain, or ring structure, and may have a heterocycle or fused ring when the fat-soluble compounds has a ring structure. The compound may be saturated or unsaturated, and has preferably a terpene structure when it has a ring structure. The compound contains preferably a sulfur atom when it has a straight or branched chain structure. Such compounds having a low molecular weight is preferably on all of those contained in the essential oil.

The essential oil is generic name of volatile oily compounds having aroma and the essential oil is obtained by steam distillation from various plants. In general, the essential oil is composed of many components and it is neither fats nor fatty oil. The main components in the essential oil are monoterpene, sesquiterpene, diterpene, and their oxidized or reduced derivatives, but small amounts of higher terpenes and non-terpenes are contained in the essential oil. In general, the essential oil is insoluble in water but soluble in alcohol, etc. About one thousand species of higher plants irregularly distributed in about 60 families can produce them, but they are distributed concentratedly in Pinales family, Umbelliferae family, Rhodomyrtus family and other couple of families.

Extracts obtained by steam distillation and expression are referred to as the essential oil, and those obtained by extraction are given several names such as pomade, concrete, absolute, resinoid, oleoresin, tincture and so forth depending on the particular extraction method.

As the essential oil employed in the present invention, there can be mentioned Eucalyptus oil, thyme oil, Labiatae oil other than thyme oil, garlic oil, welsh onion oil, scallion oil and Rutaceae oil such as lemon oil.

Eucalyptus oil is obtained by steam distilling leaves of plants belonging to Eucalyptus, and is classified into four types. One is cinede type Eucalyptus oil obtained from *Eucalyptus globulus* Labill., of which origin is Tasmania, and is mainly produced in north America, Mexico, Africa and south Spain. One of the others is piperitone phellandrene type Eucalyptus oil obtained from *Eucalyptus dives* Schauer, which is mainly produced in New South Wales and Victoria at Australia. The other one is geranyl acetate type Eucalyptus oil obtained from *Eucalyptus macarthuri* H. Deane et J. H. Maiden, which is mainly produced in southern area of New South Wales at Australia. The last one is citronellal type Eucalyptus oil obtained from *Eucalyptus citoriodora* Hook, which is mainly produced in Queensland at Australia, South Africa, Brazil, Java, and India.

Cineole type Eucalyptus oil may be obtained from leaves of *Eucalyptus globulus* Labill. by steam distillation, and contains the following components: cineole (about 70 to 80%), α-pinene, camphene, pinocarveol, pinocarvone, myatenol, berebenone, carvone, eudesmol, and $C_4$ to $C_6$ aliphatic aldehyde, and the like.

Piperitone phellandrene type Eucalyptus oil may be obtained from leaves and branches of *Eucalyptus dives* Schauer by steam distillation, and contains the following components: piperitone (about 40 to 50%), α-phellandrene (about 20 to 30%), p-cymene, camphene, dipentene, α-thujene, and the like.

Geranyl acetate type Eucalyptus oil may be obtained from leaves and branches of *Eucalyptus macarthuri* H. Deane et J. H. Maiden by steam distillation, and contains the following components: geranyl acetate (about 70%), geraniol (about 3%), eudesmol (about 16%), and other aliphatic aldehydes.

Citronellal type Eucalyptus oil may be obtained from *Eucalyptus citoriodora* Hook by steam distillation, and contains, for example, d-citronellal or l-citronellal (65 to 80%), d- or l-citronellal (15 to 20%), phellandrene, cineole, citronellye acetate, geranyl acetate, and isopulegol.

Essential oil from Labiatae is generic name of perilla oil, *Agastache rugosa* O. Kuntze oil, clary sage oil, sage oil, Nepeta oil, Catnip oil, spearmint oil, pennyroyal oil, Rosemary oil, Basil oil, Lavandin oil, Lavender oil, and other oil. Perilla oil is obtained by steam distillation from whole plant body from *Perilla frutuescenes* var. *cripsa* Decne. Froma *viridis* Makino, which is widely cultivated in Japan. The oil contains, for example, perillaldehyde (40 to 55%) of which is inherent components, α-pinene, and limonene.

*Agastache rugosa* O. Kuntze oil is obtained by steam distillation from whole plants or flowers *Agastache rugosa* O. Kuntze cultivated in temperate zone of Asia, for example, China, Japan, and Taiwan. There is a slight difference among chemical components in the composition of oil depending on the producer, and the oil produced in Taiwan comprises d-limonene, l-pulegone, l-isopulegone, other terpenoid, alcohol and ester. The oil produced in Japan comprises, for example, methyl chavicol, anisaldehyde, p-methoxy-cinnnamic aldehyde, 3-octanol, 1-octene-3-ol, and other terpenoid.

Clary sage oil is obtained by steam distillation from whole plants or flowers of *Salvia sclarea* L. The oil comprises, for example, l-linalol, linalyl acetate, scrareol, and neroridol.

Sage oil is obtained by steam distillation of dried leaves of *Salvia offensinalis* L., which are produced in Yugoslavia, Bulgaria, Turkey, France, Germany and North America. The oil comprises, for example, cineole, thujone, borneol, and camphor.

Nepeta oil and Catnip oil are obtained from the whole plants of *Nepeta cataria* L. by steam distillation, and contains nepetaric acid, nepetalactone, nepetaric anhydride, β-caryophyllene, and the like.

Mint oil is classified into Japanese mint oil, peppermint oil, and spearmint oil and pennyroyal oil. Japanese mint oil is obtained by steam distillation from the whole plants of *Menta arvensis* produced in Hokkaido, Okayama, Brazil, Paraguay and China, and comprises l-menthol, menthone, menthyl acetate, thymol, sesquiterpenoid, lower fatty acids and esters thereof.

Peppermint oil is obtained from the whole plants of *Menta piperita* var. *vulgaris* L. produced in north America, Italy, France, Bulgaria, Morocco and others by steam distillation, and comprises l-menthol, menthyl ester, menthone, menthofuran, and other components which are almost the same components as contained in Japanese mint oil.

Spearmint oil is obtained from the whole plants of *Menta spicata* Huds, var. *tenuis* (Michx) which is produced in north America, many areas of Europe by steam distillation, and comprises, for example, 1-carvone, menthone, and pulgone.

Pennyroyal oil is obtained from the whole plants of *Menta pulegium* L. var. *eriantha* by steam distillation, and comprises, for example, d-pulegone, l-menthone, d-isomenthone, piperitone, piperitone, and isopiperitenone.

Patchouli oil is obtained from leaves of *Pogostemon cablin* Benth. by steam distillation which is produced in for example, Philippines, Sumatra, and Borneo, and it comprises Patchouli alcohol, Patchoulion, Patchoulenone, cuminaldehyde and other terpenoid.

Rosemary oil is obtained from flowers, leaves or whole plants of *Rosemarinus officinalis* L. by steam distillation, and it comprises for example, borneol, bornyl acetate, camphor, and cinede.

Basil oil is obtained from flowers or whole plants of *Ocimum basilicum* L. by steam distillation, and, depending on the inherent components contained in the oil, it is classified into: a methylchavicol type containing for example, methyl-chavicol as an inherent component, linalol, and an eugenol; methyl-cinnamate type containing methyl-cinnamate as the inherent component, for example, methylchavicol, and linalol; an eugenol type containing eugenol as the inherent components; a camphor type containing d-camphor as the inherent component, a citroneral type containing citroneral as the inherent component; and a thymol type containing thymol as an inherent component.

Lavandin oil is obtained by steam distillation from flowers of *Lavendula hybrida* Reverch which is produced in south France, and it comprises, for example, linalol, linalyl acetate, linalol oxide, cinede, d-camphor, and dl-lavandulol.

Lavender oil is obtained by steam distillation from flowers of *Lavendula officinalis* Chaix. which is mainly produced in France, Italy, Hungary, southern part of ex USSR, England, north America and Australia, and comprises, for example, linalol (10 to 20%), linalyl acetate (30 to 60%), lavandulol, lavandulyl acetate, 3-octanol, α-pinene, β-pinene, limonene, cineole, and citronellal.

Several kinds of oil derived from Labiatae plants described above are preferably used in combination, and more preferably two kinds of the oil is used in combination. Particularly, lavender oil is preferably employed.

Thyme oil is obtained by steam distillation from whole plant in flowering *Thymus vulgaris* L. or dried one which is produced in, for example, south France, Italy, Turkey, Spain, Morocco and Israel, and it comprises, for example, thymol (40 to 60%), p-cymene, carvacrol, linalol, geraniol, borneol, camphene, pinene, and caryophyllene.

Garlic oil is obtained by steam distillation from bulbs of *Alium sativum* L. which is produced in Europe, northern part of China and Japan, and it comprises, for example, sulfur-containing compounds such as diallylsulfide, diallyldisulfide, allylpropyldisulfide, diallyltrisulfide, and allicin.

Welsh onion oil is obtained by stem distillation from whole plants of *Allium fistulsum* L. that is a kind of leek belonging to Liliaceae family. Scallion oil is obtained by steam distillation from whole plants of *Allium bakeri* Regel. belonging to Liliaceae family and of which origin is China.

Rutaceae oil is generic name of lime oil, sweet orange oil, grapefruit oil, neroli oil, bergamot oil, mandarin orange oil, lemon oil, Japanese pepper oil and others.

Lime oil is obtained by expression as expressed lime oil from immature fruits or mature fruits of *Citrus aurantifolia* Swing (acid lime). When peel of acid lime is subjected to steam distillation, distilled lime oil is obtained. As the components contained therein, for example, citral, methylanthranilate, bisabolene, bergaptol, limonene, and aliphatic aldehyde such as n-nonylaldehyde are mentioned.

Sweet orange oil is obtained by expression from fruits of *Cirus sinensis* Osbeck var. *brasiliensis* Tanaka. The sweet orange oil and fruit juice can be obtained separately. As the components contained therein, for example, d-limonene, citral, n-decylaldehyde, d-linalol, d-terpineol, and n-nonylalcohol are mentioned, and the content of d-limonene is more than 90%.

Grapefruit oil is obtained by expression from pericarp of *Ctrus paradisi* Macfayden (grapefruits) which is mainly produced in California, Florida, Texas, Israel and Brazil. Alternatively, when leaves or branches are subjected to steam distillation, grapefruit petitgrain oil is obtained. As the components contained therein, d-limonene (more than 90%), nootkatone as the inherent component, octylaldehyde, citral, geraniol and acetate ester thereof are mentioned.

Neroli oil is obtained by steam distillation from flowers of *Citrus aurantium* L. subsp. *amara* Engel that is mainly produced in France, Italy, Spain, Morocco and Algeria. Alternatively, orange flower concrete is obtained by extraction, and about 50% of an absolute are prepared when the concrete is extracted with alcohol. As the components contained therein, l-linalol and linalyl acetate (the sum of these two ingredients are about 35 to 40%), α-terpineol, geraniol, geranyl acetate, nerolidol (several %), and terpenes such as α-pinene, dipentene, camphene and ocimene, and sulfur-containing compounds such as methyl anthranilate and indole are mentioned. Furthermore, for example, jasmone and benzaldehyde are contained in the concrete.

Bergamot oil is obtained by expression from pericarp of *Citrus auratium* L. subsp. *bergamia* (Risso et Poit) Wright et Am. that is mainly produced in south Italy, Morocco, Tunisia, and Guinea. As the components contained therein, linalol and linalyl acetate are mentioned in a total amounts of about 55 to 75%, and monoterpene hydrocarbon, nerol, citral and the like are contained. Furthermore, bergaptene, bergamotene and methoxycoumarin are also contained as inherent components.

Mandarin oil is obtained by using sponge expression or expression from pericarp of *Cirus reticulata* Blanco var. "Mandarin". When leaves of the plant is subjected to steam distillation, mandarin petitgrain oil is obtained. It comprises d-limonene as a main component, N-methylanthranilate methyl, citral, $C_8$ to $C_{11}$ of aliphatic aldehyde of straight chain and other terpenes. Leaf oil contains N-methylanthranilate methyl as the inherent component (50 to 60%).

Lemon oil is obtained by expression from pericarp of *Citrus limone* (L.), which is mainly produced in California, Sicily, Calabria, Spain and Brazil as well as is cultivated in Japan. It comprises, for example, d-limonene, citral, octyl aldehyde, nonyl aldehyde, linalol, and geraniol.

Japanese pepper oil is obtained by homogenization and steam distillation from mature fruits of Xanthoxylum piperitum DC. As the components contained therein, dipentene (54%), geraniol and citronellol (10%), geranyl acetate and citronellyl acetate (20%), citronellal, β-phellandrene and Sanshol as the inherent components are mentioned.

Rutaceae oil is preferably used in combination of several kinds, and more preferably three kinds. Lemon oil is preferably used as Rutaceae oil.

The essentials oil containing the above-mentioned components are classified into those mainly comprising phenolic compounds, those mainly comprising sulfur-containing compounds, and those mainly comprising terpene compounds. As an example of the oil comprising phenolic compounds, thyme oil can be mentioned, and as examples of the oil comprising sulfur-containing compounds, welsh onion oil and leek oil can be mentioned. As examples of the oil comprising terpene compounds, there can be mentioned Eucalyptus oil, lavender oil and Rutaceae oil.

Specifically, as examples of the phenolic compounds contained in such oil, thymol or carvacrol in thyme oil can be mentioned. As examples of the sulfur-containing compounds, there can be mentioned diallylsulfide, diallyldisulfide, allicin and diallyltrisulfide, which are contained in garlic oil. As examples of the oil comprising terpene compounds, there can be mentioned l-camphene, d-camphene, β-eudesmol, dl-limonene (called as dipentene), which are contained in Eucalyptus oil; and d-linalol, linalyl acetate, limonene, citral and terpineol, which are contained in lavender oil and Rutaceae oil. These compounds are fat-soluble compounds having a lower molecular weight in essential oil.

In the antioxidizing composition of the present invention, essential oil is used solely or in combination. Such essential oil may be combined with at least one purified compound as described above, and the compound is not limited. As an example of the combination of essential oil with the purified compound, there can be mentioned a combination of menthol, limonene and citral as purified compounds, with Eucalyptus oil, thyme oil and lemon oil; or with a mixed oil comprising Eucalyptus oil (40%), Rutaceae oil composed of three kinds of oil belong to Rutaceae oil (30%), Labiatae oil composed of two kinds of oil belong to Labiatae oil (25%) other than, and thyme oil (5%).

Since the essential oil described above is volatile, the composition of the present invention is also volatile.

The pharmaceutical composition of the present invention is prepared by adding suitable base material and additives to the antioxidizing composition. As the base material, a water absorptive acrylic resin having a high molecular weight, a porous substance, a polysaccharide and activated charcoal are used.

As the water absorptive acrylic resin, which can absorb 400 to 800 times in volume of water based on the volume of resin is preferably used. Specifically, there can be mentioned Aquafresh (purchased from Sumitomo Fine Chemicals Inc.) and Sunfresh (Sanyo Chemical Inc.). Such resin is advantageously used because they function as a base material as well as they have water-absorption ability to continuously regulate exothermic heat caused when exposed to water together with the polysaccharide described below. Furthermore, they can adsorb and decompose basic amine gas, which is harmful for a living body, such as ammonia, trimethylamine and other amine gas.

The pharmaceutical composition may contain a coloring agent that absorbs light with a wavelength of 400 to 500 nm as an additive. As examples of such coloring agents, there can be mentioned, indigo and coloring agents absorbing violet light. The above-mentioned coloring agents are used to absorb the light having particular wavelength, and to utilize the energy of the light to enhance the energy level of molecules in the volatile composition. Then, vaporized molecules are transferred into the body through absorption route as described below.

As the activated charcoal, which is finely divided particle, commercially available one, for example, Kayamax (Nippon Kayaku Co.) may be used. The activated charcoal is adsorbed onto the antioxidizing composition, which is in the form of an oil layer on the surface of the thermoplastic resin, to form a capsule. The activated charcoal covers the surface of the antioxidizing composition to prevent the interaction between such antioxidizing compositions and to control the exothermic heat.

As an example of the porous substance, zeolite, more specifically, Zeolum (purchased from Tosoh Corp.) may be mentioned. The porous substance preferably has pore size of 3 to 10 Å, and more preferably 3 to 4 Å. Zeolite adsorbs moisture in the air to desorb the antioxidizing substances adsorbed on the base material by utilizing the adsorbing energy thereby to maintain the residence time of the antioxidizing substances at the applied sites. The porous substance having the above-mentioned pore size does not adsorb gasses except ammonia and water vapor.

As examples of the polysaccharide, cellulose or chitosan are mentioned. Commercially available cellulose may be used, and chitosan may be purchased from Koyo Chemicals, Inc. Polysaccharide has a function of regulating exothermic heat together with the above-mentioned polymer resin, in the pharmaceutical compositions of the present invention.

Furthermore, as an example of the thermoplastic resin, polyethylene can be mentioned, and as that of the water-soluble resin, polyvinyl alcohol can be mentioned. Specifically, powdered polyethylene (Sumitomo Fine Chemicals Inc.) and Goserun (Nippon Synthetic Chemicals Inc.) can be mentioned. These kinds of resin function as a carrier for adsorbing the antioxidizing compositions. Furthermore, they have a function of that binding the components of capsule, i.e. activated charcoal, base material and additives as a whole.

When the above-mentioned resin is used as the adsorbing carrier or binder, the same resin can be used for both functions, or different kinds of resin may be used.

The pharmaceutical composition of the present invention is preferably prepared as formulation for parenteral administration, because it comprises fat-soluble compounds having a low molecular weight and it is introduced into lymphatic duct, and more preferably as percutaneous formulation.

As percutaneous routes for absorbing drugs, the following routes are mentioned: a route which passes through corneum to reach capillaries in papillary layer in subcticular bindweb, and a route which passes through sebaceous gland of attached organs to reach blood vessels or lymphatic ducts. In either route, drugs are delivered through capillary or capillary lymphatic ducts into systemic circulation to express their pharmacological action. When drugs are absorbed through percutaneous route, lymphotropic activity of the drug is higher when they are administrated via percutaneous route than per os or parenteral route, although their absorption rate varies depending on the structure of them or physicochemical properties.

Skin provides a route to excrete metabolites out of body, and it functions as barrier to prevent the invasion of extraneous material, and it is composed of epiderm and corium. Sebaceous membrane is formed on corneum of epiderm, and corium has papipallry layer and reticular layer.

Sebaceous membrane on epiderm is the first absorption surface for the essential oil, and sebaceous membrane is an emulsion membrane. Sebaceous membrane prevents invasion of bacteria, and regulates the body temperature. When the body temperature increases, the emulsion membrane becomes oil-in-water (o/w) type to accelerate water vapor to lower the temperature by heat of vaporization. In contrast, when the prevention of the body temperature loss is intended, the membrane becomes water-in-oil (w/o) type to prevent sweating. Since the absorption of the essential oil on the emulsion membrane is prevented when the membrane is (o/w), it must be (w/o). Therefore, the alcohol type of components in the essential one mixed to accelerate vaporization of water on the surface of epiderm to enhance drug absorption on the membrane.

In papillary layer, artery-vein inosculation of peripheral vessels and capillary lymphatic ducts are incorporated, and substance exchange or gas exchange is carried out. In such substance exchange field, there exist carrier substances for drug such as lipid or protein, and the essential oil, which passes through sebaceous membrane to reach inside of papillary layer, flows into veins or lymphatic ducts. Then the drug is delivered to lymph nodes or peripheral tissues through veins or lymphatic ducts or both, and they are incorporated into cells via their lipid bilayer in deliver or terminal of delivery.

The pharmaceutical composition of the present invention is formulated as follows: the antioxidizing composition is adsorbed on a polymer resin to form an oil film, and then charcoal powder is absorbed on the oil film to obtain a granule having an outer surface made of the charcoal. Thus obtained dust granule is inserted between two sheet materials, and all edges are bound by heat pressing to form a percutaneous agent.

The above-mentioned sheet material is preferably composed of paper or non-woven fabric, and more preferably non-woven fabric, because vaporized molecules in essential oil easily permeates the sheet material when the components in the essential oil become gaseous state.

The pharmaceutical composition comprising the antioxidizing composition thus obtained as the percutaneous sheet material is administrated by allowing it to contact with skin. For example, the percutaneous sheet material is fastened by appropriate means, for example, double-sided pressure sensitive adhesive tape, on the back center of a collar of a shirt for human to allow the sheet material to contact with back of cervix. By fastening the sheet material as described above, the vaporized compositions of the present invention reaches the skin through the non-woven fabric, to be absorbed via sebaceous membrane. Then they are transferred into blood vessels or lymphatic ducts. In order to administrate to animals, for example, the sheet material is fastened inside of a collar by using the double-sided pressure sensitive adhesive tape to be administrated percutaneously from the back cervix in the same manner as for human. In human, the sheet material may be allowed to touch shoulder; hip or any other sites other than neck by fastening the sheet material with suitable means inside of clothes to administrate.

The fastened percutaneous sheet material may be exchanged every couple of days to maintain a certain effect.

As described above, since the pharmaceutical composition of the present invention is lymphotropic, it is effective for aquired immunodeficiency syndrome (AIDS) or autoimmune disease. It is known that HIV infects T cell in charge of cellular immunity, that is helper T cell to decrease immunity. CD4, which is a firstly reported as human helper T cell marker, is a glycoprotein expressed on T cell. T cells, which express only CD4 occupies about 65% of the peripheral T cells and they are referred to as CD4+ T hereinbelow, have mainly helper T cell properties. Since CD4+ binds to HIV, it is known that CD4 functions as a receptor.

HIV infected T cell expressing CD4 has 100 times higher sensitivity than normal cells, and therefore these cells generate active oxygen, that is free radical.

Since free radical decreases the number of normal helper T cells to increase relatively that of suppressor T cells, this leads to a decrease in the ratio of helper T cell number/suppressor T cell number to progress AIDS. In such situation appeared, it generates both qualitative and quantitative abnormalities in cytokine network, and promotes histodialysis in lymph node, which is referred to as reactive hyperplasia.

When the pharmaceutical composition of the present invention is administrated percutaneously to the patients or patient animals with the above-mentioned symptoms, the essential oil contained in the pharmaceutical compositions make HIV infected CD4+ T cell cytostatic. Accordingly, such essential oil components are introduced into lymphatic ducts to deliver lymph nodes. Then the components prevent further histodialysis of lymphatic tissues, and they maintain the cells in cytostatic situation so as to function the repair and regeneration ability of the body itself. Therefore, resistance to the AIDS of patients or patient animals is enhanced. That is, the pharmaceutical composition of the present invention has also immunopotentiation activities.

Furthermore, since the administration of the pharmaceutical composition of the present invention can be easily done by attaching the sheet form agent, and the administration can be easily stopped by detaching the sheet material from the fastened site. Only the essential oil derived from natural sources or their components are vaporized to be transferred in the body, any serious side effects are not observed.

EXAMPLES

The present invention will now be described by the following examples in detail. However, the present invention is not limited to the examples.

Example 1

(1) Preparation of Antioxidizing Composition-1

An antioxidizing composition-1 of the present invention was prepared by mixing the essential oils in the amounts shown in Table 2 as the principal constituent. All flavors and fragrances used here were purchased from Ogawa Perfumes Inc.

TABLE 2

| Recipe of antioxidizing composition-1 | |
| --- | --- |
| Kinds of materials | weight (%) |
| Menthol | 19.8 |
| Limonene | 3.2 |
| Citral | 1.6 |
| Eucalyptus oil | 5.6 |
| Thyme oil | 1.6 |
| Lemon oil | 1.6 |
| Total | 33.4 |

(2) Preparation of Pharmaceutical Compositions Comprising the Antioxidizing Composition-1.

The pharmaceutical composition of the present invention is prepared by mixing the antioxidizing composition-1 with principle constituents in amount weight shown in Table 3.

TABLE 3

| Pharmaceutical composition comprising the antioxidizing composition-1 | |
| --- | --- |
| Materials | weight (mg) |
| Principal constituent | 33.4 |
| Sunfresh (Sumitomo Fine Chemical Inc.) | 55.6 |
| Zeolum (Tosoh Corp.) | 15.8 |
| Chitosan (Koyo Chemical Co.) | 8 |
| Kayamax (Nippon Chemical Inc.) | 39.6 |
| Indigo | trace |
| Powdery polyethylene (Sumitomo Fine Chemical Inc.) | 47.6 |
| Total | 200.0 |

Each essential oil shown in the above-mentioned (1) was respectively mixed with the powdery polyethylene resin to form oil film on the resin surface. Then the resin covered with essential oil and activated charcoal were mixed together to absorb the charcoal to form a carbon-coated capsule.

Separately from that, Sunfresh, Zeolum and Chitosan were mixed to form a base material. Then the carbon-coated capsule containing the essential oil, which was made by the above-mentioned procedure, was added to the base material together with indigo, and mixes to prepare the pharmaceutical composition of the present invention.

Two hundreds mg of thus obtained pharmaceutical composition of the present invention was covered with a piece of cotton cloth, and then sandwiched between two non-woven sheet materials. Then, all peripheral edges of the sheet materials were bonded by heat pressing to form a percuateous absorption agent.

Example 2

(1) Preparation of Antioxidizing Composition-2

An antioxidizing composition-1 of the present invention was prepared by mixing the essential oils in amount shown in Table 4 as the principal constituent. All flavors and fragrances used here were purchased from Ogawa Perfumes Inc.

TABLE 4

Recipe of antioxidizing composition-2

| Essential oil | Ratio (%) | weight (mg) |
| --- | --- | --- |
| Eucalyptus oil | 40 | 0.44 |
| Rutaceae oil | 30 | 0.33 |
| Labiatae oil | 25 | 0.275 |
| Thyme oil | 5 | 0.055 |
| Total | 100 | 1.1 |

(2) Preparation of Pharmaceutical Compositions Comprising Antioxidizing Composition-2

The pharmaceutical composition of the present invention is prepared by mixing the antioxidizing composition-2 with principle constituents in amounts shown in Table 5.

TABLE 5

Pharmaceutical composition comprising antioxidizing composition-1

| Materials | weight (mg) |
| --- | --- |
| Principal constituent | 1.1 |
| Water soluble resin having high molecular weight | 52.1 |
| Polyvinyl alcohol | 83.5 |
| Synthetic Zeolite | 10.3 |
| Activated charcoal | 5.3 |
| Thermoplastic resin | 52.1 |
| L-Menthol | 15.6 |
| Total | 220 |

Each essential oil shown in the above-mentioned (1) was respectively mixed with the powdery polyethylene resin to form oil film on the surface of the resin. Then the resin covered with essential oil and the activated charcoal were mixed together adsorb the charcoal to form a carbon-coated capsule.

Separately from that, Aquafresh, Zeolum and PVA were mixed to form a base material. Then the carbon-coated capsule containing the essential oil, which was made by the above-mentioned procedure, was added to the base material, and mixed to prepare the pharmaceutical composition-2 of the present invention.

Two hundreds and twenty mg of thus obtained pharmaceutical composition of the present invention was covered with a piece of cotton cloth, and then sandwiched between two non-woven sheet materials. Then, all peripheral edges of the sheet materials were bonded by heat pressing to form the percutaneous absorption agent.

Example 3

Test Result for FIV Spontaneously Infected Cats (1) Animals

As an experiment animal model for AIDS, a feline immunodeficiency virus, which is abbreviated as FIV, infected cat appearing AIDS (n=1), and two FIV infected cats but not appearing AIDS (n=2) were used.

(2) Administration Procedure

The percutaneous absorption sheets prepared in the Preparation (2) were fastened inside of collars by using double-sided pressure sensitive adhesive tape, and the collars were put on the neck of cats so as to allow the percutaneous sheets to touch the skin. The percutaneous sheets were exchanged every three days.

(3) Administration Schedule

The sheet-form agents were administrated percutaneously for 4 weeks by fastening inside of the collars, and then nothing was administrated for next 2 weeks. After that, a sheet-form placebo was administrated percutaneously for 4 weeks, and then the agent was again administrated percutaneously for 1 week.

Placebo was prepared from Sunfresh as the water-soluble resin having high molecular weight, powdery polyethylene resin as thermoplastic resin, and Kayamax as activated charcoal. In the placebo, any essential oil and a coloring agent are not contained.

(4) Items to be Measured

Items to be measured are the number of lymphocytes, the number of T cell expressing sole CD4 (CD4+), the number of T cell expressing sole CD8 (CD8+), the ratio of CD4+/CD8+, and IgG level.

(5) Result

Test results were shown in Table 5 and FIG. 1. As shown in Table 5 and FIG. 1, the number of lymphocytes, CD4+, CD8+ were increased, and the IgG level was enhanced during the agent was administrated. However, when the administration of the agent was stopped, those numbers and the level were decreased.

Example 4

Suppression of Disorder Caused by Active Oxygen (1) Experiment Animals

Two groups of SPF cats are used as four per group.

(2) Administration Procedure

Percutaneous absorption agent prepared in the preparation (2) was fastened inside of collars of the cats, and the collars were put on the necks of them so as to allow the agent to touch the skin of back cervix. The agents were exchanged every three days.

(3) Administration Schedule and Evaluation

Treatment group received the fastened agent inside of the collar as described above for two weeks. Control group received nothing.

Both groups received 1 mg/kg of methylene blue in every 8 hours, Heinz body formation ratios in erythrocytes after 40 hours from methylene blue administration were compared.

After methylene blue administration, placebo was administrated to the groups in the same manner as the agent for four weeks. Then, the agent was administrated for one week. As the placebo, a sheet without the composition of the present invention was used.

(4) Result

Figure 2:
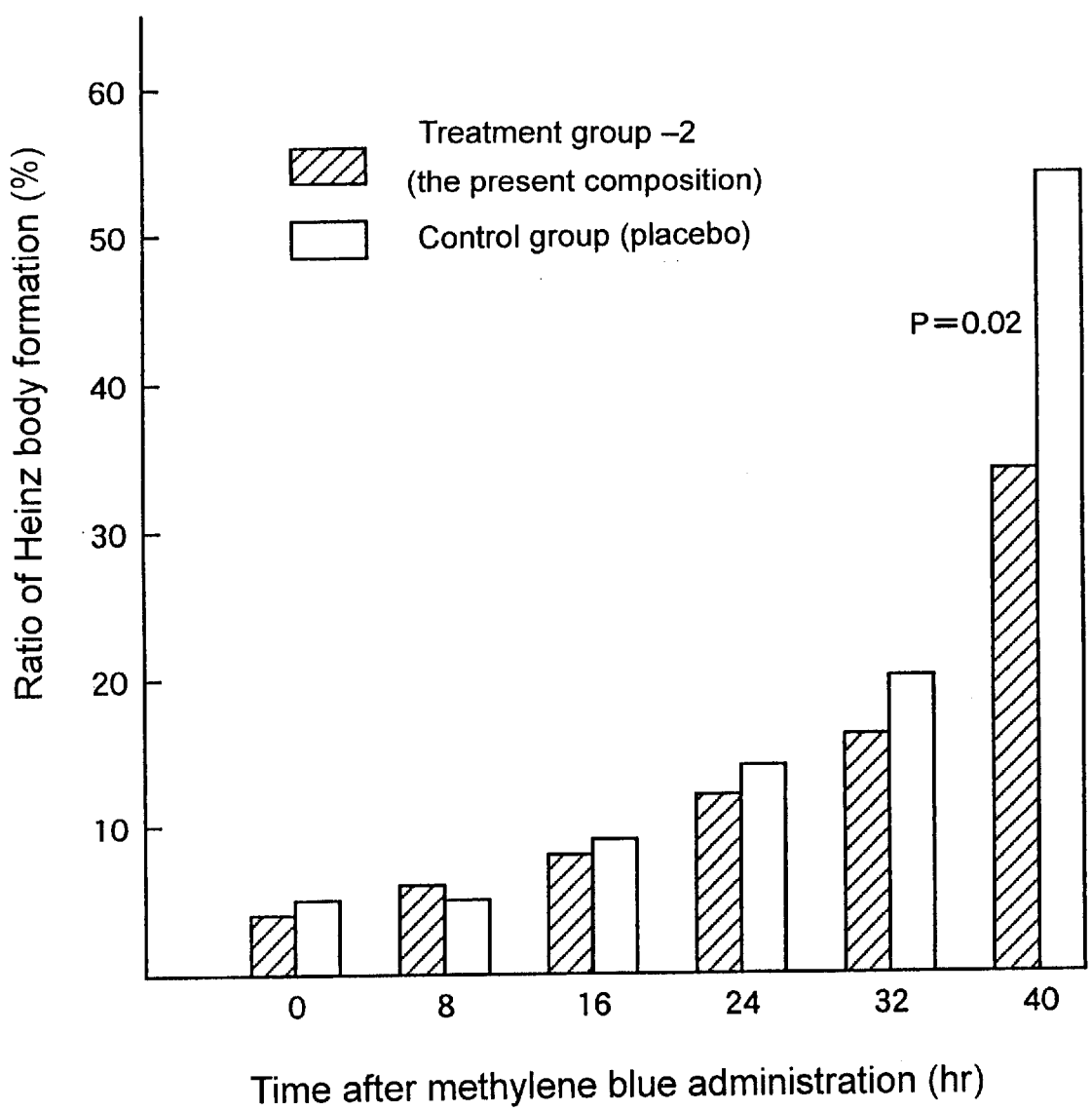
FIG. 2 is a graph showing the suppression effect for oxidation disorder caused by methylene blue administration. The composition of the invention and placebo are administrated to SPF cats by using gas formulation through the skin of back of cervix. Then methylene blue is administrated at a dose of 1 mg/kg by every 8 hours, and Heinz body formation ratios in erythrocytes are compared after 40 hours from the beginning.

Results were shown in FIG. 2. As shown in FIG. 2, it was demonstrated that Heinz body formation ratio was significantly suppressed, in the groups received the composition of the present invention.

As described above, according to the present invention, there are provided the antioxidizing composition comprising fat-soluble compounds having a low molecular weight in the essential oil, the pharmaceutical compound comprising antioxidizing composition and the process thereof. When the pharmaceutical composition is formulated to percutaneous absorption agent, the composition is delivered to lymph through sebaceous route to delete free radicals in lymph nodes, and increases the number of T cells expressing particular glycoproteins to show immunopotentiation activity.

As mentioned above, it is demonstrated that the composition of the present invention is effective for immune diseases, especially AIDS.

INDUSTRIAL APPLICABILITY

The present invention is utilized in the field of pharmaceuticals. Particularly, essential oil derived from natural sources in the composition of the present invention is absorbed percutaneously to be transferred directly into a body, it is utilized for curing immune disease, particularly AIDS.

What is claimed is:

1. A sheet-form pharmaceutical preparation for gas dosage comprising a pharmaceutical composition-containing mixture which is sandwiched between two sheet-form materials; said mixture comprising
    (i) a carbon-coated pharmaceutical composition comprising at least three kinds of carbon-coated particles (A), (B) and (C), wherein
       (A) is prepared by allowing a water-insoluble powdery thermoplastic resin to adsorb one essential oil selected from Rutaceae plant oil group (a) consisting of lime oil, orange oil, grapefruit oil, bergamot oil, mandarin oil, lemon oil, which are obtained by expression; and neroli oil and Japanese pepper oil, which are obtained by seam distillation, and then coating the essential oil-adsorbed powdery thermoplastic resin with finely divided activated carbon particles;
       (B) is prepared by allowing a water-insoluble powdery thermoplastic resin to adsorb one essential oil selected from Labiatae plant oil group (b) consisting of Perilla oil, *Agastache rugosa* O, Kuntze oil, Clary sage oil, Sage oil, Thyme oil, Nepeta oil, Japanese Mint oil, Peppermint oil, Spearmint oil, Pennyroyal oil, Patchouli oil, Rosemary oil, Basil oil, Lavandin oil, and Lavender oil, all of which are obtained by steam distillation, and coated with finely divided activated carbon particles;
       (C) is prepared by allowing a water-insoluble powdery thermoplastic resin to adsorb essential oil selected from Myrtaceae plant oil group (c) consisting of Clove oil, Pimenta oil, Bay oil, Cineole-type Eucalyptus oil, geranyl acetate-type Eucalyptus oil, and Citronellal-type Eucalyptus oil, all of which are obtained by steam distillation, and coated with finely divided activated carbon particles,
    (ii) a water-absorptive resin having a high-molecular-weight which is capable of absorbing 400 to 800 times its volume of water based on the volume of the water-absorptive resin,
    (iii) a porous substance,
    (iv) a polysaccharide, and
    (v) said water-insoluble powdery thermoplastic resin or a water-soluble thermoplastic resin.

2. The pharmaceutical preparation for gas dosage as claimed in claim 1, wherein said mixture further comprises a coloring agent, which absorbs light with a particular wavelength.

3. A sheet-form pharmaceutical preparation for gas dosage comprising a pharmaceutical composition-containing mixture which is sandwiched between two sheet-form materials; said mixture comprising
    (i) a carbon-coated pharmaceutical composition comprising at least three kinds of carbon-coated particles (A), (B) and (C) according to claim 1,
    (ii) a water-absorptive acrylic resin as a water-absorptive resin having a high-molecular-weight which is capable of absorbing 400 to 800 times its volume of water based on the volume of the water-absorptive acrylic resin,
    (iii) zeolite as a porous substance,
    (iv) chitosan as a polysaccharide,
    (v) powdery polyethylene as the water-insoluble thermoplastic resin, and
    (vi) indigo as a coloring agent which absorbs light with a particular wavelength.

4. A sheet-form pharmaceutical preparation for gas dosage comprising a pharmaceutical composition-containing mixture which is sandwiched between two sheet-form materials; said mixture comprising,
    (i) at least three kinds of carbon coated particles, which are selected from the group consisting of (A), (B) and (C) according to claim 1, together with carbon coated particles which are prepared by allowing powdery polyethylene as a water-insoluble powdery thermoplastic resin to adsorb L-menthol, and then coating the L-menthol-adsorbed powdery polyethylene with finely divided activated carbon particles,
    (ii) a water-absorptive acrylic resin as a water-absorptive resin having a high-molecular-weight which is capable of absorbing 400 to 800 times in volume of water based on the volume of the water-absorptive acrylic resin,
    (iii) zeolite as a porous substance, and
    (iv) polyvinyl alcohol as a water-soluble thermoplastic resin.

* * * * *

UNITED STATES PATENT AND TRADEMARK OFFICE
CERTIFICATE OF CORRECTION

PATENT NO.    : 6,190,685 B1
DATED         : February 20, 2001
INVENTOR(S)   : Karita It is certified that error appears in the above-identified patent and that said Letters Patent is hereby corrected as shown below:

Column 1,
Line 25, delete "(.$O_2^-$)" insert -- ($\cdot O_2^-$) --;
Line 25, delete "(.OH)" insert ($\cdot$OH) --;
Line 31, delete "(.OOH)" insert -- ($\cdot$OOH) --;
Line 36, delete "R. + .OOH" insert -- R$\cdot$ + $\cdot$OOH -- ;
Line 38, delete "(.OO$^-$)" insert ($\cdot$OO$^-$) --;
Line 48, delete "2.$O_2^-$" insert -- 2$\cdot O_2^-$ --.

Column 2,
Lines 17, 18, 20, 21, 36 and 37 of each, delete ".OH" insert -- $\cdot$OH --;
Lines 31, 32 and 37 of each, delete ".$O_2^-$" insert -- $\cdot O_2^-$ --

Column 5,
Line 34, delete "myatenol, berebenone" insert -- myrtenol, verbenone.

Column 6,
Line 4, delete, "citronellal" insert -- citronellol --;
Line 5, delete "citronellye" and insert -- citronellyl --;
Line 60, delete "piperitone" insert -- piperitenone --.

Column 7,
Line 7, delete "methyl-chavicol" insert -- methyl chavicol --;
Lines 12 and 13, delete "citroneral" insert -- citronellal --;
Line 18, delete "cinede" insert -- cineole --.
Line 60, delete "Cirus" insert -- Citrus --;
Line 67, delete "Ctrus" insert -- Citrus --.

UNITED STATES PATENT AND TRADEMARK OFFICE
CERTIFICATE OF CORRECTION

PATENT NO. : 6,190,685 B1
DATED : February 20, 2001
INVENTOR(S) : Karita

It is certified that error appears in the above-identified patent and that said Letters Patent is hereby corrected as shown below:

Column 8,
Line 31, delete "Cirus" insert -- Citrus --.

Column 15,
Line 43, delete "seam" insert -- steam --;
Line 49, delete "O," insert -- O. --.

Signed and Sealed this

Sixteenth Day of October, 2001

Attest:

*Nicholas P. Godici*

NICHOLAS P. GODICI
*Attesting Officer*     *Acting Director of the United States Patent and Trademark Office*